(12) United States Patent
Shieh et al.

(10) Patent No.: US 8,124,763 B2
(45) Date of Patent: Feb. 28, 2012

(54) PROCESS FOR THE SYNTHESIS OF 5-(METHYL-1H-IMIDAZOL-1-YL)-3-(TRIFLUOROMETHYL)-BENZENEAMINE

(75) Inventors: Wen-Chung Shieh, Berkeley Heights, NJ (US); Joseph McKenna, Nazareth, PA (US)

(73) Assignee: Novartis AG, Basel (CH)

( * ) Notice: Subject to any disclaimer, the term of this patent is extended or adjusted under 35 U.S.C. 154(b) by 1050 days.

(21) Appl. No.: 11/915,671

(22) PCT Filed: Jun. 7, 2006

(86) PCT No.: PCT/US2006/022155
§ 371 (c)(1),
(2), (4) Date: Nov. 27, 2007

(87) PCT Pub. No.: WO2006/135641
PCT Pub. Date: Dec. 21, 2006

(65) Prior Publication Data
US 2008/0188656 A1 Aug. 7, 2008

Related U.S. Application Data

(60) Provisional application No. 60/688,977, filed on Jun. 9, 2005, provisional application No. 60/705,590, filed on Aug. 4, 2005.

(51) Int. Cl.
*C07D 401/14* (2006.01)
(52) U.S. Cl. .................................... 544/328
(58) Field of Classification Search ............ 544/328
See application file for complete search history.

(56) References Cited

U.S. PATENT DOCUMENTS
6,323,366 B1    11/2001    Wolfe et al.
(Continued)

FOREIGN PATENT DOCUMENTS
WO    00/05199    2/2000
(Continued)

OTHER PUBLICATIONS

Klapars et al., "A General and Efficient Copper Catalyst for the Amidation of Aryl Halides and the N-Arylation of Nitrogen Heterocycles." J. Am. Chem. Soc., vol. 123, pp. 7727-7729 (2001).

(Continued)

*Primary Examiner* — Deepak Rao
(74) *Attorney, Agent, or Firm* — Stephen E. Johnson

(57) ABSTRACT

The present invention provides a new method of making compounds of formula (I):

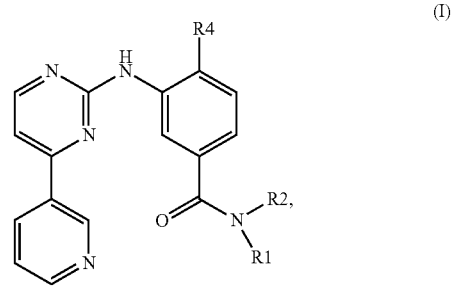

wherein
R1 is mono- or polysubstituted aryl;
R2 is hydrogen, lower alkyl or aryl; and
R4 is hydrogen, lower alkyl or halogen.

5 Claims, No Drawings

U.S. PATENT DOCUMENTS

| | | | |
|---|---|---|---|
| 6,395,916 | B1 | 5/2002 | Buchwald et al. |
| 2003/0236413 | A1 | 12/2003 | Cellier et al. |

FOREIGN PATENT DOCUMENTS

| | | |
|---|---|---|
| WO | WO 00/05199 | 2/2000 |
| WO | 2004/005281 | 1/2004 |
| WO | WO 2004/005281 | 1/2004 |

OTHER PUBLICATIONS

Suzuki et al., "A Novel Non-Acidic Method for the Preparation of 2,2,2-Trifluoro-1-(3-nitrophenyl)ethanone and 1-Nitro-3-trifluoromothylbenzene, Versatile Starting Materials for trifluoromethyl-Containing Aromatic Compounds," Synthesis. pp. 1353-1354 (1995).

Purohit et al., "Synthesis and Characterization of Oligodeoxynucleotides Containing the Major DNA Adducts Formed by 1,6- and 1,8-Dinitropyrene," Organic Letters, vol. 2, No. 13. pp. 1871-1874 (2000).

Mukkanti et al., "Selective and Squential Reduction of Nitroaromatics by Montmorillonitesilylaminepalladium(II) Complex." Tetrahedron Letters, vol. 30, No. 2, pp. 251-252 (1989).

Shackelford et al., "Electrophilic tetraalkylammonium Nitrate Nitration. II. Improved Anhydrous Aromatic and Heteroaromatic Mononitration with Tetramethylammonium Nitrate and Triflic Anhydride, Including Selected Microwave Examples," J. Org. Chem., vol. 66, pp. 267-275. (2003).

Zoltewict, J.A., "New Directions in Aromatic Nucleophilic Substitution," Topics in Current Chemistry, vol. 59, pp. 33-64 (1975).

Wang et al., "Monoacylation of unprotected symmetrical diamines with resin-bound benzoic acids" Tetrahedron Letters, vol. 45, No. 35, pp. 6645-6648 (2004).

Klapars et al., "A General and Efficient Copper Catalyst for the Amidation of Aryl Halides and the N-Arylation of Nitrogen Heterocycles," J. Am. Chem. Soc., vol. 123, pp. 7727-7729 (2001).

Suzuki et al., "A Novel Non-Acidic Method for the Preparation of 2,2,2-Trifluoro-1-(3-nitrophenyl)ethanone and 1-Nitro-3-trifluoromethylbenzene, Versatile Starting Materials for trifluoromethyl-Containing Aromatic Compounds," Synthesis, pp. 1353-1354 (1995).

Wolfe et al., "Room Temperature Catalytic Amination of Aryl Iodides," J. Org. Chem., vol. 62, pp. 6066-6068 (1997).

Kiyomori et al., "An Efficient Copper-Catalyzed Coupling of Aryl Halides with Imidazoles," Tetrahedron Letters, vol. 40, pp. 2657-2660 (1999).

Baenziger et al., "Practical Synthesis of 8α-Amino-2,6-dimethylergoline: An Industrial Perspective," Organic Process Research & Development, vol. 1, pp. 395-406 (1997).

Zilberman J., "One-Step Preparation of some 3-Substituted Anisoles," Organic Process Research & Development, vol. 7, pp. 303-305 (2003).

Purohit et al., "Synthesis and Characterization of Oligodeoxynucleotides Containing the Major DNA Adducts Formed by 1,6- and 1,8-Dinitropyrene," Organic Letters, vol. 2, No. 13, pp. 1871-1874 (2000).

Ali et al., "An Improved Method for the Palladium-Catalyzed Amination of Aryl Iodides," J. Org. Chem., vol. 66, pp. 2560-2565 (2001).

Mukkanti et al., "Selective and Squential Reduction of Nitroaromatics by Montmorillonitesilylaminepalladium(II) Complex," Tetrahedron Letters, vol. 30, No. 2, pp. 251-252 (1989).

Subba Rao et al., "Efficient selective hydrodebromination of aryl bromides by montmorillonitesilylaminepalladium(II) chloride," Journal of Organometallic Chemistry, vol. 367, Issue 3, pp. C29-C31 (1989) Abstract only.

Grondard et al., "Convenient Syntheses of Racemic 2-(3-Nitrophenyl)Propanoic Acid and 2-(3-Aminophenyl)Propanoic Acid," Synthetic Communications, vol. 27(3), pp. 425-430 (1997).

Shackelford et al., "Electrophilic tetraalkylammonium Nitrate Nitration. II Improved Anhydrous Aromatic and Heteroaromatic Mononitration with Tetramethylammonium Nitrate and Triflic Anhydride, Including Selected Microwave Examples," J. Org. Chem., vol. 68, pp. 267-275 (2003).

Mellor et al., "Improved Nitrations Using Metal Nitrate—Sulfuric Acid System," Tetrahedron, vol. 56, pp. 8019-8024 (2000).

Zoltewicz, J.A., "New Directions in Aromatic Nucleophilic Substitution," Topics in Current Chemistry, vol. 59, pp. 33-64 (1975).

Hofmann, A., Helv. Chim. Acta, Volumen XXX, Fasciculus I, pp. 44-51 (1947).

Möller F., in Houben-Weyl. Bd. Nov. 1, pp. 854 (1957).

Hofmann, A.W., Chem. Ber. 14, pp. 275 (1881).

Wang et al., "Monoacylation of unprotected symmetrical diamines with resin-bound benzoic acids," Tetrahedron Letters, vol. 45, No. 35, pp. 6645-6648 (2004).

PROCESS FOR THE SYNTHESIS OF 5-(METHYL-1H-IMIDAZOL-1-YL)-3-(TRIFLUOROMETHYL)-BENZENEAMINE

This application is a 371 of PCT/US06/22155 filed Jun. 7, 2006 which claims the benefit of U.S. Provisional Application No. 60/688,977, filed Jun. 9, 2005, and U.S. Provisional Application No. 60/705,590, filed Aug. 4, 2005.

BACKGROUND OF THE INVENTION

The present invention provides a new method of making compounds of formula (I):

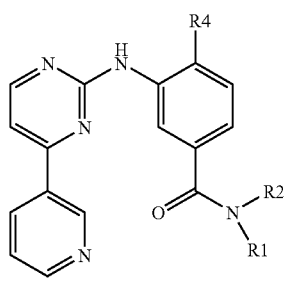

(I)

wherein

R1 is mono- or polysubstituted aryl;

R2 is hydrogen, lower alkyl or aryl; and

R4 is hydrogen, lower alkyl, or halogen.

Compounds of formula (I) have been disclosed in W. Breitenstein et al., WO 04/005281 which published on Jan. 15, 2004, the disclosure of which is incorporated by reference. A preferred compound of formula (I) is 4-methyl-3-[[4-(3-pyridinyl)-2-pyrimidinyl]amino]-N-[5-(4-methyl-1H-imidazol-1-yl)-3-(trifluoromethyl)phenyl]benzamide (Ia). Compounds of formula (I) have been shown to inhibit one or more tyrosine kinases, such as c-Abl, Bcr-Abl, the receptor tyrosine kinases PDGF-R, Flt3, VEGF-R, EGF-R and c-Kit. As such, compounds of formula (I) can be used for the treatment of certain neoplastic diseases, such as leukemia.

Previous synthesis of compounds of formula (I), and specifically (Ia), involves a hydrolysis of an ethyl ester to a carboxylic acid, which is then reacted with an aniline, and employing diethylcyanophosphonate as a coupling agent as shown in Scheme 1.

Scheme 1

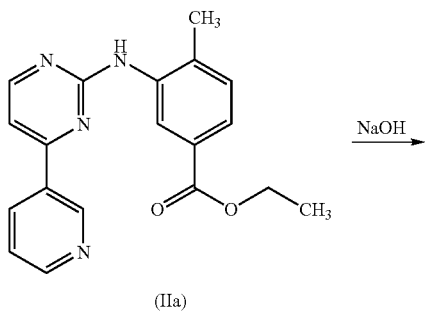

(IIa)

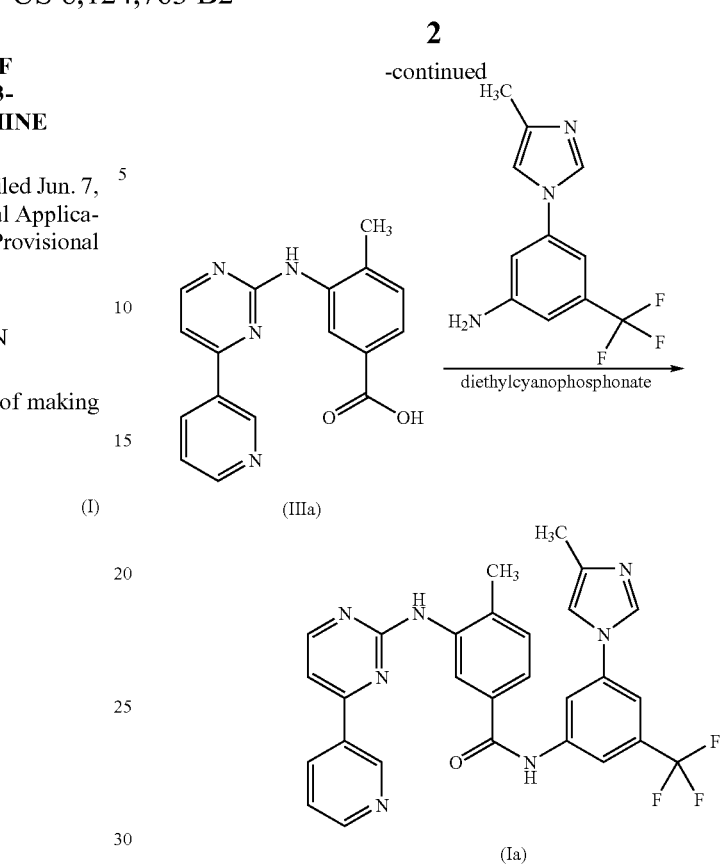

This process gives low and inconsistent yields. Furthermore, diethylcyanophosphonate is an expensive reagent. Thus, there is a need for an alternate process that is cheaper, consistent, efficient, and produces compounds (I) in high yields.

It is an object of this invention to provide for an alternative process to make compounds of formula (I) efficiently with high and consistent yields.

It is a further object of this invention to make compounds of formula (I) from lower cost reagents.

It is a still further object of this invention to provide for a process to make compounds of formula (I) utilizing safer reagents.

The present invention overcomes the problems encountered in the previous synthesis described in Scheme 1 and typically resulted in an increased overall yield from 54-86%.

SUMMARY OF THE INVENTION

The present invention provides a new method of making compounds of formula (I):

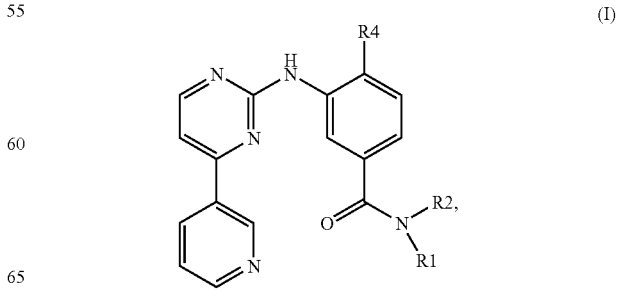

(I)

comprising the following reaction:

Scheme 2

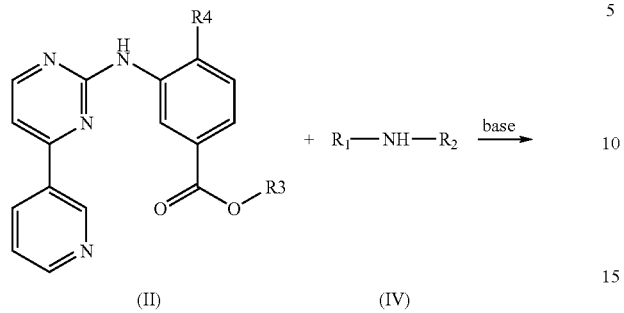

wherein
R1 is substituted or unsubstituted aryl;
R2 is hydrogen, lower alky or aryl;
R4 is hydrogen, lower alkyl or halogen; and
R3 is lower alkyl, phenyl, phenyl-lower alkyl or substituted phenyl.

Direct condensation of ester (II) with aniline (IV) is catalyzed by a base, such as potassium tert-butoxide to make compounds of formula (I). The process is carried out at temperature between −50° C. to 50° C. in an organic solvent of tetrahydrofuran, dimethylformamide, toluene or N-methylpyrrolidinone.

DETAILED DESCRIPTION OF THE INVENTION

The general reaction scheme of the invention can be illustrated as follows:

Scheme 2

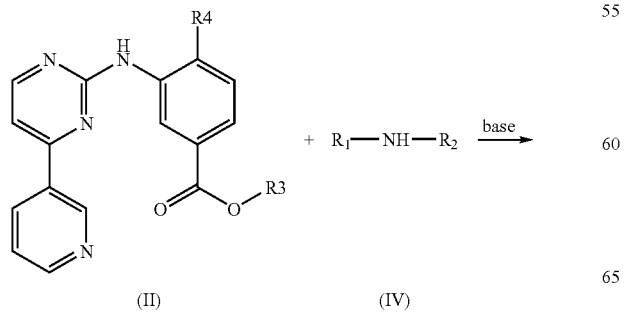

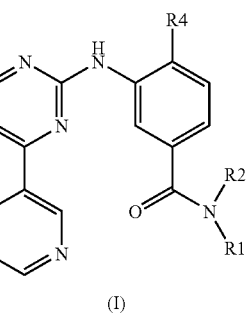

wherein
R1 is substituted or unsubstituted aryl;
R2 is hydrogen, lower alky or aryl;
R4 is hydrogen, lower alkyl or halogen; and
R3 is lower alkyl, phenyl, phenyl-lower alkyl or substituted phenyl.

Direct condensation of ester (II) with aniline (IV) can be catalyzed by a strong base such as potassium tert-butoxide to make compounds of formula (I) in good yield and high purity without any chromatography or recrystallization purification. Other bases, such as metal hydride, bulkyl alkyl lithium, metal alkoxide, metal bis(trimethylsilyl)amide or lithium dialkylamide, can also be used. The metal can be lithium, sodium or potassium. The process is carried out at temperature between −50° C. to 50° C. in an organic solvent of tetrahydrofuran, dimethylformamide, toluene or N-methylpyrrolidinone.

In a preferred embodiment, the process comprises the following reaction:

Scheme 3

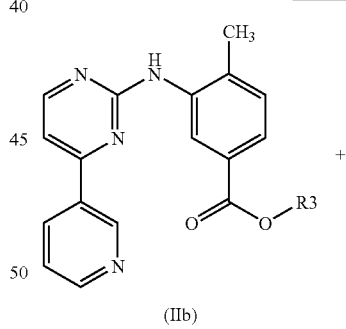

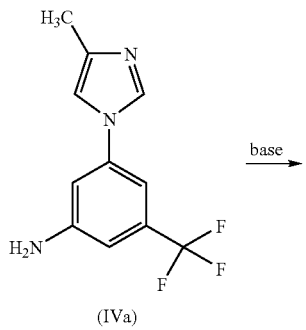

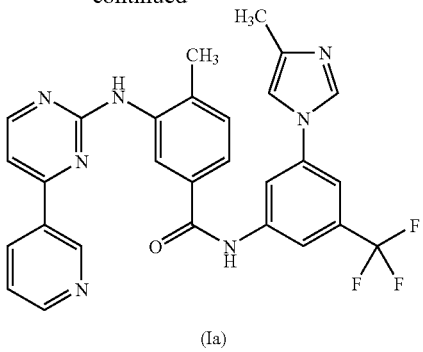

(Ia)

wherein R3 is lower alkyl, phenyl, phenyl-lower alkyl or substituted phenyl.

The compound of formula (IVa) can be prepared using processes disclosed in patent applications U.S. Ser. No. 60/688,920 and Ser. No. 60/688,976, both entitled "Process for the Synthesis of Organic Compounds", which were filed concurrently herewith. The disclosures of those applications are incorporated herein by reference.

In the most preferred embodiment, the process comprises the following reaction:

Scheme 4

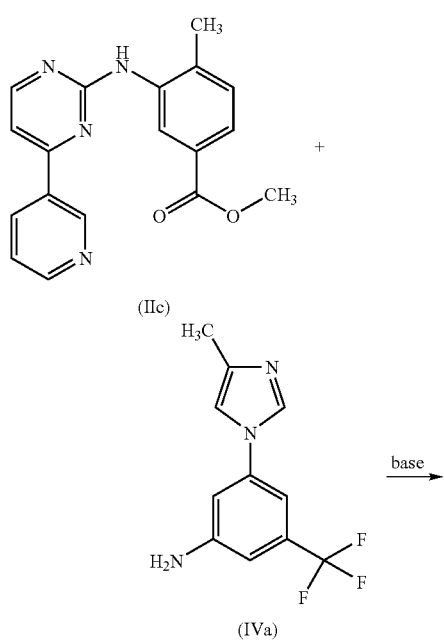

Lower alkyl comprises 1-6 carbon atoms, and is linear or branched; preferred lower alkyl moieties are butyl, such as n-butyl, sec-butyl, isobutyl, tert-butyl, propyl, such as n-propyl or isopropyl, ethyl or methyl. Particularly preferred lower alkyl moieties are methyl, ethyl, n-propyl or tert-butyl.

An aryl group is an aromatic radical which is bound to the molecule via a bond located at an aromatic ring carbon atom of the radical. In a preferred embodiment, aryl is an aromatic radical having 6-14 carbon atoms, especially phenyl, naphthyl, tetrahydronaphthyl, fluorenyl or phenanthrenyl, and is unsubstituted or substituted by one or more, preferably up to three, especially one or two substituents, wherein the substituents are heterocyclyl groups comprising one, two, three ring nitrogen atoms, one oxygen atom or one sulfur atom; other substituents on aryl include disubstituted amino, halogen, lower alkyl, substituted lower alkyl, lower alkenyl, lower alkynyl, phenyl, etherified hydroxy, esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, heterocyclyl, a mono- or bicyclic heteroaryl group or lower alkylene dioxy bound at adjacent C-atoms of the ring, such as methylene dioxy. According to a preferred embodiment, aryl is phenyl, naphthyl or tetrahydronaphthyl, which in each case is either unsubstituted or independently substituted by one or two substituents selected from the group consisting of halogen, especially fluorine, chlorine or bromine; hydroxy etherified by lower alkyl, e.g., by methyl, by halogen-lower alkyl, e.g., trifluoromethyl, or by phenyl; lower alkylene dioxy bound to two adjacent C-atoms, e.g., methylenedioxy, lower alkyl, e.g., methyl or propyl; halogen-lower alkyl, e.g., trifluoromethyl; hydroxy-lower alkyl, e.g., hydroxymethyl or 2-hydroxy-2-propyl; lower alkoxy-lower alkyl; e.g., methoxymethyl or 2-methoxyethyl; lower alkoxycarbonyl-lower alkyl, e.g., methoxy-carbonylmethyl; lower alkynyl, such as 1-propynyl; esterified carboxy, especially lower alkoxycarbonyl, e.g., methoxycarbonyl, n-propoxy carbonyl or isopropoxy carbonyl; N-mono-substituted carbamoyl, in particular, carbamoyl monosubstituted by lower alkyl, e.g., methyl, n-propyl or isopropyl; di-lower alkylamino, e.g., dimethylamino or diethylamino; lower alkylene-amino, e.g., pyrrolidino or piperidino; lower oxaalkylene-amino, e.g., morpholino, lower azaalkylene-amino, e.g., piperazino, acylamino, e.g., acetylamino or benzoylamino; lower alkylsulfonyl, e.g., methylsulfonyl; sulfamoyl; and phenylsulfonyl.

Halogen is fluorine, chlorine, bromine, or iodine, especially fluorine, chlorine, or bromine.

The following examples more particularly illustrate the present invention, but do not limit the invention in any way.

Example 1

Synthesis of Compound of Formula (Ia)

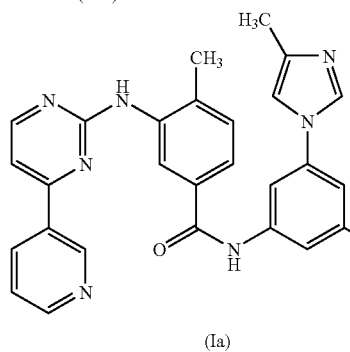

(Ia)

As used in this application, except as otherwise expressly provided herein, each of the following terms shall have the meaning set forth below.

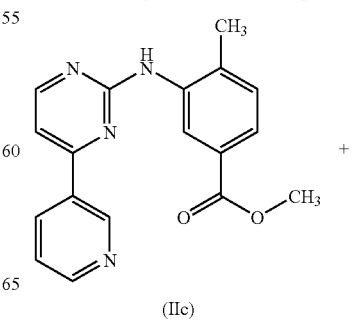

(IIc)

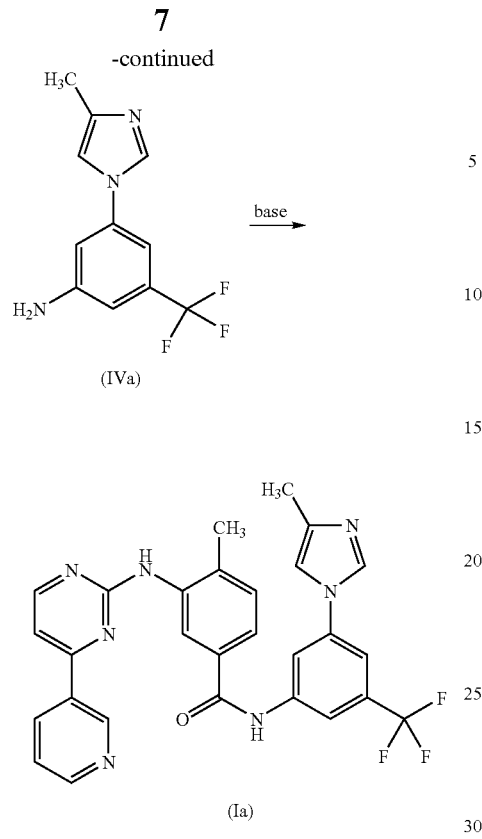

(IVa)

(Ia)

To a 1-L flask, equipped with a mechanical stirrer, temperature sensor, reflux condenser, addition funnel and nitrogen inlet-outlet under a nitrogen atmosphere at 23° C. is charged with compounds (IIc) (16 g), (IVa) (12 g) and THF (300 mL). The mixture is stirred for 15 minutes at 23° C. and cooled to −20° C. to −15° C. A solution of 1 M potassium t-butoxide in THF (275 mL) is added at −20° C. to −10° C. After the addition, the mixture is warmed to 18-23° C. When the reaction is complete according to HPLC, the mixture is cooled to 5° C. A solution of 15% aqueous sodium chloride (500 mL) is added to the mixture, maintaining temperature below 15° C. Product is extracted into isopropyl acetate (500 mL) and washed in sequence with 15% aqueous sodium chloride solution (500 mL) and water (500 mL). The organic phase is distilled under atmospheric pressure at an internal temperature of 75-85° C. until the residual volume is about 200 mL. The resulting suspension is cooled to 70±5° C. and charged with ethanol (250 mL) and water (30 mL). The mixture is heated to reflux (78° C.) for 1 hour and then cooled to −10° C. to −15° C. The suspension is stirred for an additional 30 minutes at −10° C. to −15° C. Any solid is collected by filtration, rinsed with cold (5° C.) ethanol (85 mL) and dried under vacuum (10-20 torr) at 55-60° C. with a nitrogen bleed (8-16 hours) to obtain AMN107 (17.4 g, 67% yield) as a white solid.

$^1$H NMR 300 MHz, DMSO-$d_6$), δ 10.5 (s, 1H), 9.15 (s, 1H), 9.05 (s, 1H), 8.60 (s, 1H), 8.45 (d, 1H), 8.35 (d, 1H), 8.22 (d, 2H), 8.10 (d, 2H), 7.65 (m, 2H), 7.45 (m, 4H), 2.25 (s, 3H), 2.05 (s, 3H).

What is claimed is:

1. A process for the preparation of compounds of formula (I)

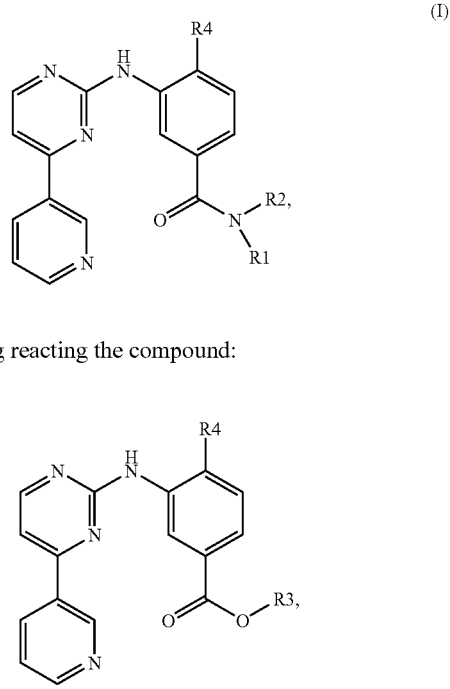

comprising reacting the compound:

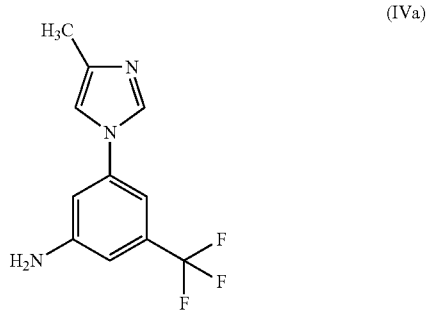

with 5-(4-Methyl-1H-imidazol-1-yl-3-(trifluoromethyl)-benzenamine of structure (IVa):

(IVa)

wherein

R₁ 5-(4 methyl-1H-imidazol-1-yl)-3-(trifluoromethyl)-phenyl;

R₂ is hydrogen;

R₄ is hydrogen, lower alkyl or halogen; and

R³ is lower alkyl, phenyl, phenyl-lower alkyl or substituted phenyl, and wherein the process is catalyzed by a base selected from the group consisting of metal hydride, bulky alkyl lithium, metal alkoxide, metal bis(trimethylsilyl)amide and lithium dialkylamide, in an organic solvent.

2. A process for the preparation of a compound of the formula (Ia)

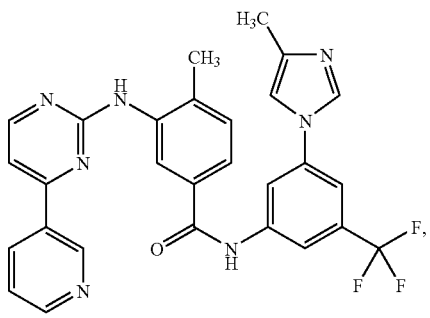

comprising reacting the compound:

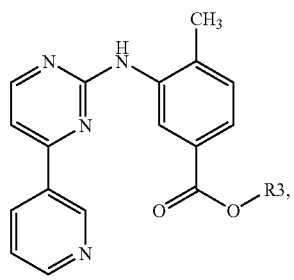

wherein R3 is lower alkyl, phenyl, phenyl-lower alkyl or substituted phenyl, with the compound 5-(4-methyl-1H-imidazol-1-yl)-3-(trifluoromethyl)-benzenamine of the structure (IVa):

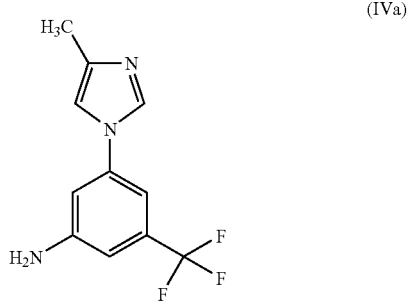

and wherein the process is catalyzed by a base selected from the group consisting of metal hydride, bulky alkyl lithium, metal alkoxide, metal bis(trimethylsilyl)amide and lithium dialkylamide, in an organic solvent.

3. The process of claim 1 or 2, wherein the metal is selected from the group consisting of lithium/sodium and potassium.

4. The process of claim 3, wherein the base is potassium tert-butoxide.

5. The process of claim 3; wherein the organic solvent is selected from the group of tetrahydrofuran, dimethylformamide, toluene and N-methylpyrrolidone.

* * * * *

UNITED STATES PATENT AND TRADEMARK OFFICE
CERTIFICATE OF CORRECTION

| | | |
|---|---|---|
| PATENT NO. | : 8,124,763 B2 | |
| APPLICATION NO. | : 11/915671 | |
| DATED | : February 28, 2012 | |
| INVENTOR(S) | : Shieh et al. | |

It is certified that error appears in the above-identified patent and that said Letters Patent is hereby corrected as shown below:

In the Specification

Column 4, Line 28 should be corrected as follows:

Replace "bulkyl" with "bulky"

The line should read: Other bases, such as metal hydride, bulky alkyl lithium,

Signed and Sealed this
Twenty-sixth Day of May, 2015

Michelle K. Lee
*Director of the United States Patent and Trademark Office*